United States Patent [19]

Mersch

[11] Patent Number: 5,760,894
[45] Date of Patent: *Jun. 2, 1998

[54] LIQUID SAMPLE ANALYSIS IN AN OPTICAL FOURIER TRANSFORM SYSTEM

[75] Inventor: Steven Henry Mersch, Germantown, Ohio

[73] Assignee: Point Source, Inc., Germantown, Ohio

[*] Notice: The term of this patent shall not extend beyond the expiration date of Pat. No. 5,559,596.

[21] Appl. No.: 706,523

[22] Filed: Sep. 4, 1996

Related U.S. Application Data

[63] Continuation-in-part of Ser. No. 387,484, Feb. 13, 1995, Pat. No. 5,559,596.

[51] Int. Cl.[6] .......................... G01N 21/01; G01N 1/10
[52] U.S. Cl. .................... 356/246; 356/244; 422/100
[58] Field of Search .................... 356/244, 246, 356/128, 361, 346; 422/55–58, 61, 100, 101, 102, 82.09, 82.11, 57, 82.05, 82.06; 435/805; 436/169, 170, 165, 175, 177, 178, 180, 518, 524, 531

[56] References Cited

U.S. PATENT DOCUMENTS

| 4,233,029 | 11/1980 | Columbus | 422/100 |
|---|---|---|---|
| 4,713,349 | 12/1987 | Levin | 436/515 |
| 4,735,487 | 4/1988 | Thorwirth et al. | 350/162.12 |
| 4,826,319 | 5/1989 | Namba et al. | 210/198.2 |
| 4,906,439 | 3/1990 | Grenner | 422/100 |
| 4,956,150 | 9/1990 | Henry | 422/102 |
| 5,039,617 | 8/1991 | McDonald et al. | 422/57 |
| 5,051,237 | 9/1991 | Grenner et al. | 422/57 |
| 5,100,626 | 3/1992 | Levin | 422/100 |
| 5,151,752 | 9/1992 | Oono et al. | 356/128 |
| 5,565,729 | 10/1996 | Faris et al. | 313/103 |
| 5,590,538 | 1/1997 | Hsu et al. | 62/51 |
| 5,603,351 | 2/1997 | Cherukuri et al. | 137/597 |

*Primary Examiner*—Frank G. Font
*Assistant Examiner*—Michael P. Stafira
*Attorney, Agent, or Firm*—Killworth, Gottman, Hagan & Schaeff, L.L.P.

[57] ABSTRACT

A liquid sample is placed into a sample container which is placed into an optical fourier transform system to produce an image representative of characteristics of the liquid sample and particles within the liquid sample. The container, formed of an optical material, includes microchannels which continuously increase in path length from a minimum path length at a first side to a maximum path length at a second side. In one embodiment, the microchannels are immediately adjacent one another while in another embodiment the microchannels are spaced from one another by a defined spacing. By spacing the microchannels from one another, two fourier transform images are generated within the system, one a refracted image and the other a diffracted image. In addition, by forming the second sides of the spaced microchannels at an acute angle relative to the plane of the microchannels, a reflected fourier transform image can also be generated within the system. The fourier transform images, refracted, diffracted or reflected, formed by the samples in the noted containers are one dimensional. Two dimensional fourier transform images can be generated by forming a plurality of parallel chemical strips within the microchannels and orienting the chemical strips generally perpendicular to the microchannels.

26 Claims, 7 Drawing Sheets

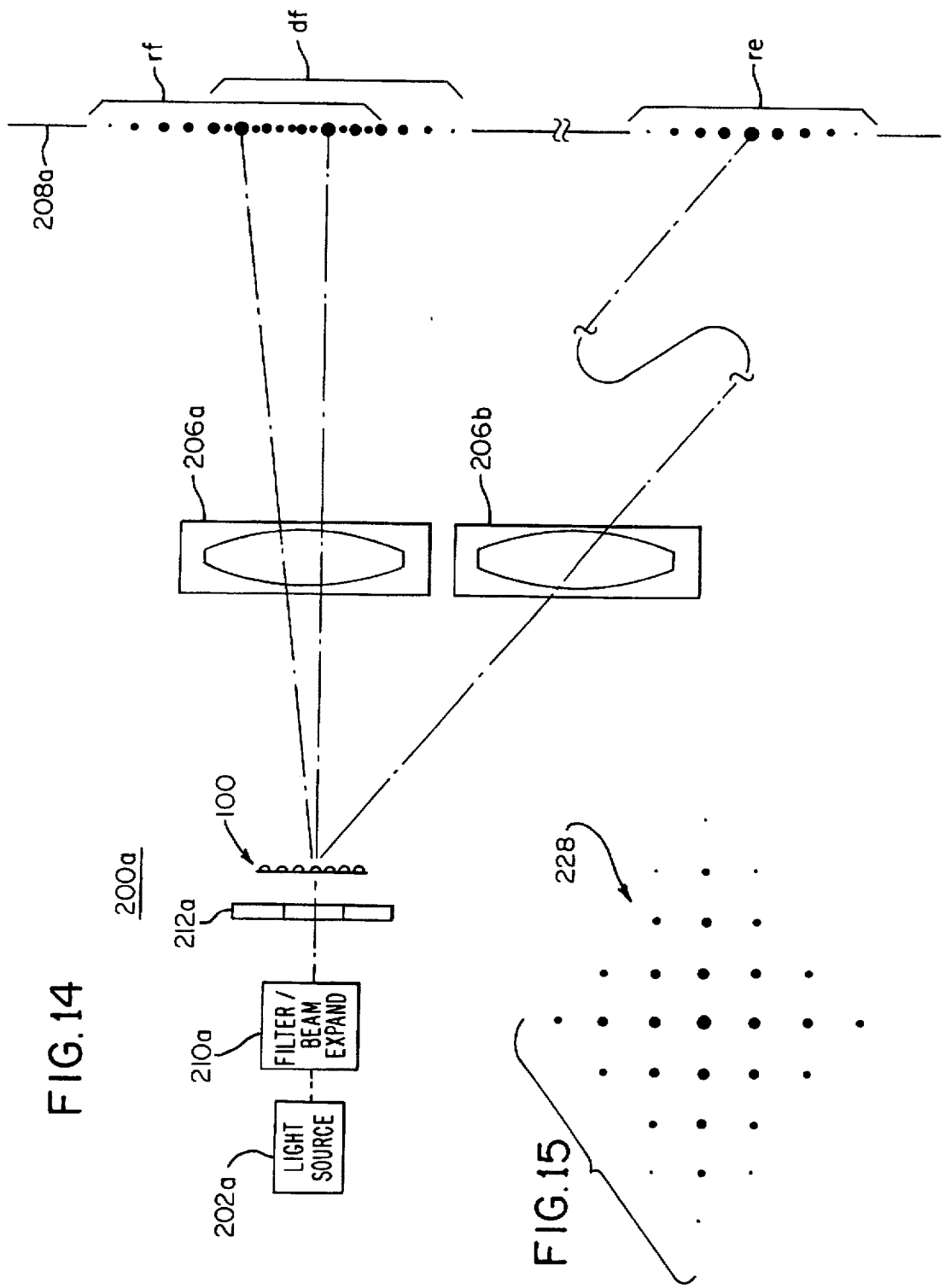

5,760,894

LIQUID SAMPLE ANALYSIS IN AN OPTICAL FOURIER TRANSFORM SYSTEM

CROSS-REFERENCE TO RELATED APPLICATIONS

This application is a continuation-in-part of U.S. patent application Ser. No. 08/387,484, filed Feb. 13, 1995, and entitled LIQUID SAMPLE ANALYSIS BY OPTICAL FOURIER TRANSFORM IMAGING now U.S. Pat. No. 5,559,596, the disclosure of which is hereby incorporated by reference.

BACKGROUND OF THE INVENTION

The present invention relates in general to the analysis of liquid samples and, more particularly, to a method and apparatus wherein liquid sample containers receive samples to be analyzed in an optical fourier transform system with resulting optical fourier transforms being used to determine characteristics of the liquid samples and particles contained within the liquid samples. While the present invention is generally applicable to the analysis of a wide variety of liquids including, for example, industrial and biological liquids, it will be described herein with reference to the in vitro analysis of biological liquids for which it is initially to be used.

The analysis of biological liquids is vital to medical practice not only for diagnosis and treatment of diseases but also for medical research and development of new treatments and medicines. Such analysis is normally performed by laboratories using sophisticated equipment and test procedures. Unfortunately, typical laboratory equipment is very expensive, bulky and requires highly trained and skilled technicians for proper operation. In addition, to ensure adequate quantities of biological liquids for analysis, relatively large samples, often of dangerous liquids, are forwarded to the laboratories and excesses must be properly disposed of by the laboratories.

Such expensive, bulky and complicated laboratory equipment is not practical for use in home health monitoring applications, in remote or hostile environments such as third world rural areas, in manned space programs, in general practice doctors' offices and in many others. It is, thus, apparent that there is a need for a simplified arrangement for performing analysis of biological liquids. Preferably, such an arrangement would be small, inexpensive and able to perform analysis of biological liquids with small quantities of the liquids. Ideally, once tested, liquid samples would be easily disposable, preferably contained within a disposable sample container.

SUMMARY OF THE INVENTION

This need is met by the method and apparatus of the present invention wherein a liquid sample to be analyzed is placed into a sample container which is in turn placed into an optical fourier transform system, preferably a portable system, which produces a fourier image or images representative of characteristics of the liquid sample and particles within the liquid sample.

A small portion, for example one drop, of a liquid sample is received in a sample container with the liquid sample entering open-ended microchannels in the container by capillary action. The microchannels are parallel to one another, lie in a common plane and each defines a plurality of optical paths having a range of path lengths which enable optical fourier analysis of the liquid sample within the container. Preferably, the optical paths continuously increase in path length from a minimum path length at a first side of each microchannel to a maximum path length at a second side of each microchannel. The container is formed of an optical material such that the liquid sample in the microchannels forms a grating when placed into the optical fourier transform system. Accordingly, the fourier transform image generated within the system is characteristic of the liquid sample forming the grating for the system.

In one embodiment of the liquid sample container, the microchannels are immediately adjacent one another while in another embodiment, the microchannels are spaced from one another by a defined spacing, for example the spacing can be approximately equal to the maximum path length of the microchannels. By spacing the microchannels from one another, two fourier transform images are generated within the system, one a refracted image and the other a diffracted image. Typically, the refracted and diffracted fourier transform images partially overlap one another in the fourier image plane. In addition, by forming the second sides of the spaced microchannels at an acute angle relative to the plane of the microchannels, a reflected fourier transform image can also be generated within the system.

The fourier transform images, refracted, diffracted or reflected, formed by the samples in the noted containers are one dimensional. Two dimensional fourier transform images can be generated by forming a plurality of parallel chemical strips within the microchannels and orienting the chemical strips generally perpendicular to the microchannels.

The liquid sample container is preferably formed of two plates of optical material, preferably optical acrylic, which may be coated or otherwise treated to make it non-hydrophilic to prevent the loss of moisture from liquid samples. A first one of the plates has an array of microgrooves formed into a first surface of the plate. A second plate defines a surface for engaging the first plate to close the microgrooves and turn them into the open-ended microchannels of the container. Preferably, the surface of the second plate is coated to define the chemical strips for containers which are to produce two dimensional fourier transform images. The two plates are aligned relative to one another by pins on one plate which are received in matching apertures in the other plate. The two plates are secured to one another by an appropriate adhesive. The first plate also defines a handle for holding and handling the container.

In accordance with one aspect of the present invention, a liquid sample container comprises a sample receiving and holding housing defining a plurality of parallel open-ended optical microchannels lying adjacent one another within a plane to form an optical lenticular array. Each of the optical microchannels defines a plurality of optical paths which continuously increase in optical path length from a minimum path length at a first side of the microchannel to a maximum path length at a second side of the microchannel. The housing permits illumination of a liquid sample received within the microchannels along an optical axis intersecting the plane at an angle other than zero degrees.

The sample receiving and holding housing may comprise a first plate having a plurality of parallel microgrooves formed in a first surface thereof, and a second plate at least coextensive with a portion of the first plate having the microgrooves and defining a surface for engaging the portion of the first plate to close the microgrooves to thereby define the open-ended optical microchannels. Preferably, the plurality of microchannels have first and second open ends, and the first plate extends beyond the first end of the plurality of parallel open-ended optical microchannels to define a liquid sample loading member for receiving a liquid sample to be loaded into the microchannels. The first plate may also define an open vent channel for venting the second open ends of the plurality of microchannels. For two dimensional analysis, the container further comprises a plurality of parallel chemical strips formed within the optical lenticular array and oriented generally perpendicular thereto. The chemical strips may be formed of an antigen.

In accordance with another aspect of the present invention, a liquid sample container comprises a sample receiving and holding housing defining a plurality of parallel open-ended microchannels extending in a first direction and lying within a plane and a plurality of parallel chemical strips formed within the microchannels and oriented generally perpendicular to the microchannels. The housing permits illumination of a liquid sample received within the microchannels along an optical axis intersecting the plane at an angle other than zero degrees. The sample receiving and holding housing may comprise a first plate having a plurality of parallel microgrooves formed in a first surface thereof, and a second plate at least coextensive with a portion of the first plate having the microgrooves and defining a surface for engaging the portion of the first plate to close the microgrooves to thereby define the open-ended microchannels, the surface of the second plate being coated to define the chemical strips.

In accordance with yet another aspect of the present invention, a liquid sample container comprises a sample receiving and holding housing defining a plurality of parallel open-ended microchannels extending in a first direction and lying within a plane. The microchannels are spaced from one another by a defined spacing and the housing permits illumination of a liquid sample received within the microchannels along an optical axis intersecting the plane at an angle other than zero degrees. Each of the microchannels may define a plurality of optical paths which continuously increase in optical path length from a minimum path length at a first side of the microchannel to a maximum path length at a second side of the microchannel with the defined spacing is approximately equal to the maximum path length. For expanded analysis potential, the second sides of the microchannels are acutely angled relative to the plane and the container may further comprise a plurality of parallel chemical strips formed within the microchannels and oriented generally perpendicular to the microchannels.

In accordance with still another aspect of the present invention, a liquid sample container comprises a sample receiving and holding housing defining a plurality of substantially equally spaced parallel open-ended microchannels extending in a first direction and lying within a plane. Each of the microchannels defines a plurality of optical paths which continuously increase in optical path length from a minimum path length at a first side of the microchannel to a maximum path length at a second side of the microchannel which is acutely angled relative to the plane. The housing permits illumination of a liquid sample received within the microchannels along an optical axis intersecting the plane at an angle other than zero degrees. For expanded analysis potential, the container may further comprise a plurality of parallel chemical strips formed within the microchannels and oriented generally perpendicular to the microchannels.

In accordance with an additional aspect of the present invention, a method of analyzing a liquid sample comprises the steps of: depositing a liquid sample to be analyzed into a liquid sample receiving and holding housing having a plurality of parallel open-ended microchannels lying within a plane and forming a lenticular array, the microchannels being spaced from one another by a defined spacing; illuminating the liquid sample receiving and holding housing along an optical axis intersecting the plane within which the plurality of parallel open-ended microchannels lie at an angle greater than zero relative to the plane; focusing light received from the liquid sample receiving and holding housing onto a fourier transform plane; and, detecting at least one optical fourier transform at the fourier transform plane.

The method of analyzing a fluid sample further comprises the step of determining characteristics of the fluid sample by analyzing the at least one optical fourier transform. The step of detecting at least one optical fourier transform may comprise the step of detecting a refracted optical fourier transform and a diffracted optical fourier transform.

For expanded one dimensional analysis, the microchannels define a plurality of optical paths which continuously increase in optical path length from a minimum path length at a first side of the microchannel to a maximum path length at a second side of the microchannel which is acutely angled relative to the plane and the step of detecting at least one optical fourier transform comprises the step of detecting a reflected optical fourier transform. For two dimensional analysis, the liquid sample receiving and holding housing further comprises a plurality of parallel chemical strips formed within the lenticular array and oriented generally perpendicular thereto and the step of detecting at least one optical fourier transform comprises the step of detecting at least one two dimensional optical fourier transform.

It is, thus, an object of the present invention to provide an improved method and apparatus for quickly and inexpensively analyzing a liquid sample; to provide an improved method and apparatus for quickly and inexpensively analyzing a liquid sample by means of an optical fourier transform system; and, to provide an improved method and apparatus for quickly and inexpensively analyzing a liquid sample by means of an optical fourier transform system wherein a liquid sample to be analyzed is received in a lenticular array liquid sample container which is inserted into an optical fourier transform system to generate refracted, diffracted and/or reflected one and/or two dimensional fourier transform images for analysis of the liquid contained within the sample container.

Other objects and advantages of the invention will be apparent from the following description, the accompanying drawings and the appended claims.

BRIEF DESCRIPTION OF THE DRAWINGS

FIG. 14 illustrates an optical fourier transform system capable of forming refracted, diffracted and reflected optical fourier transform images using the lenticular design of FIG. 12;

FIG. 15 illustrates a two dimensional fourier transform image formed in accordance with the present invention.

DETAILED DESCRIPTION OF THE INVENTION

Figure 1:
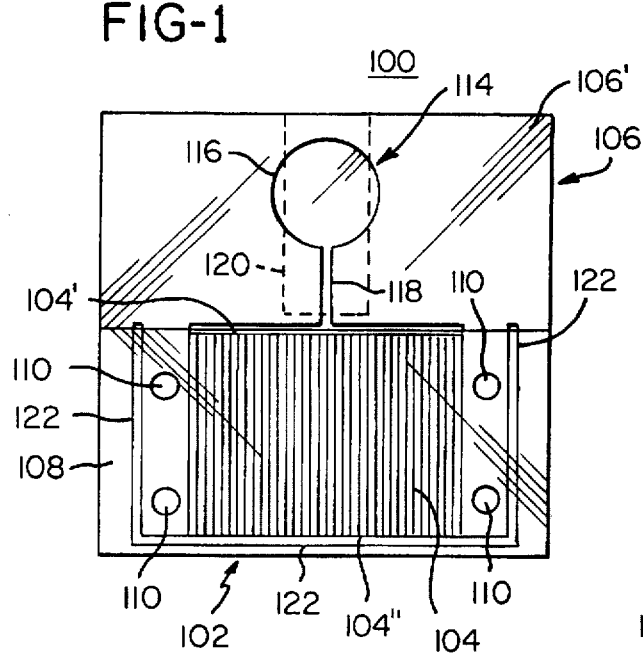
FIG. 1 is a front view of a liquid sample container of the present invention.
Figure 2:
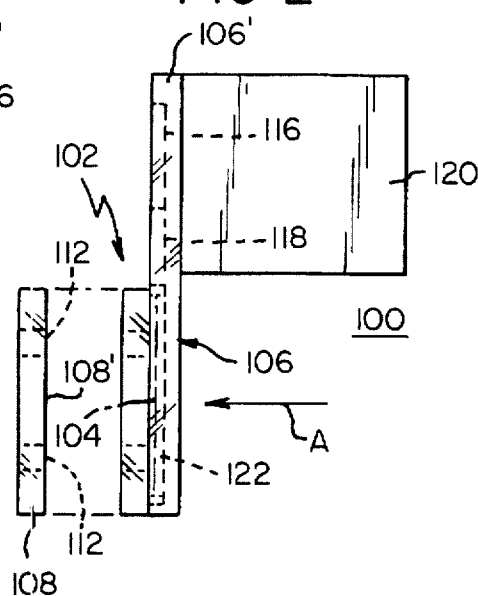
FIG. 2 is a side view of the liquid sample container of FIG. 1 showing the two part construction of the illustrated embodiment.
Figure 6:
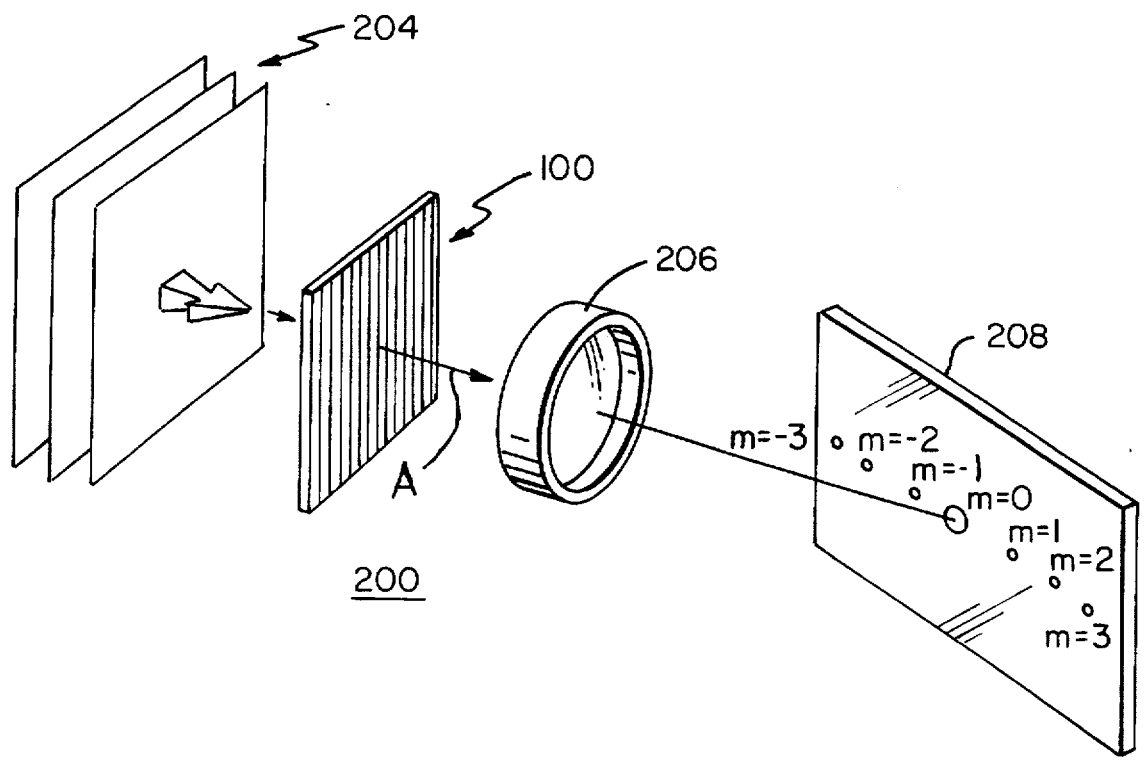
FIGS. 6 and 7 schematically illustrate operation of an optical fourier transform system.
Figure 7:
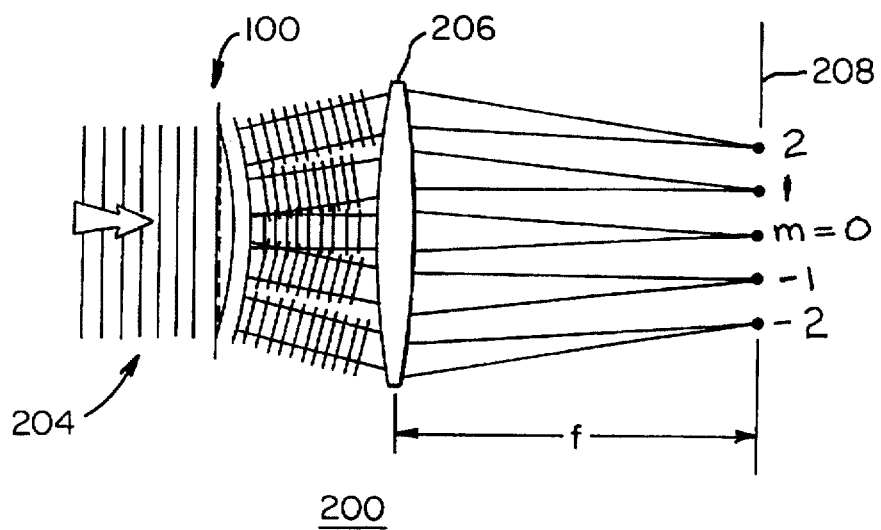
Figure 8:
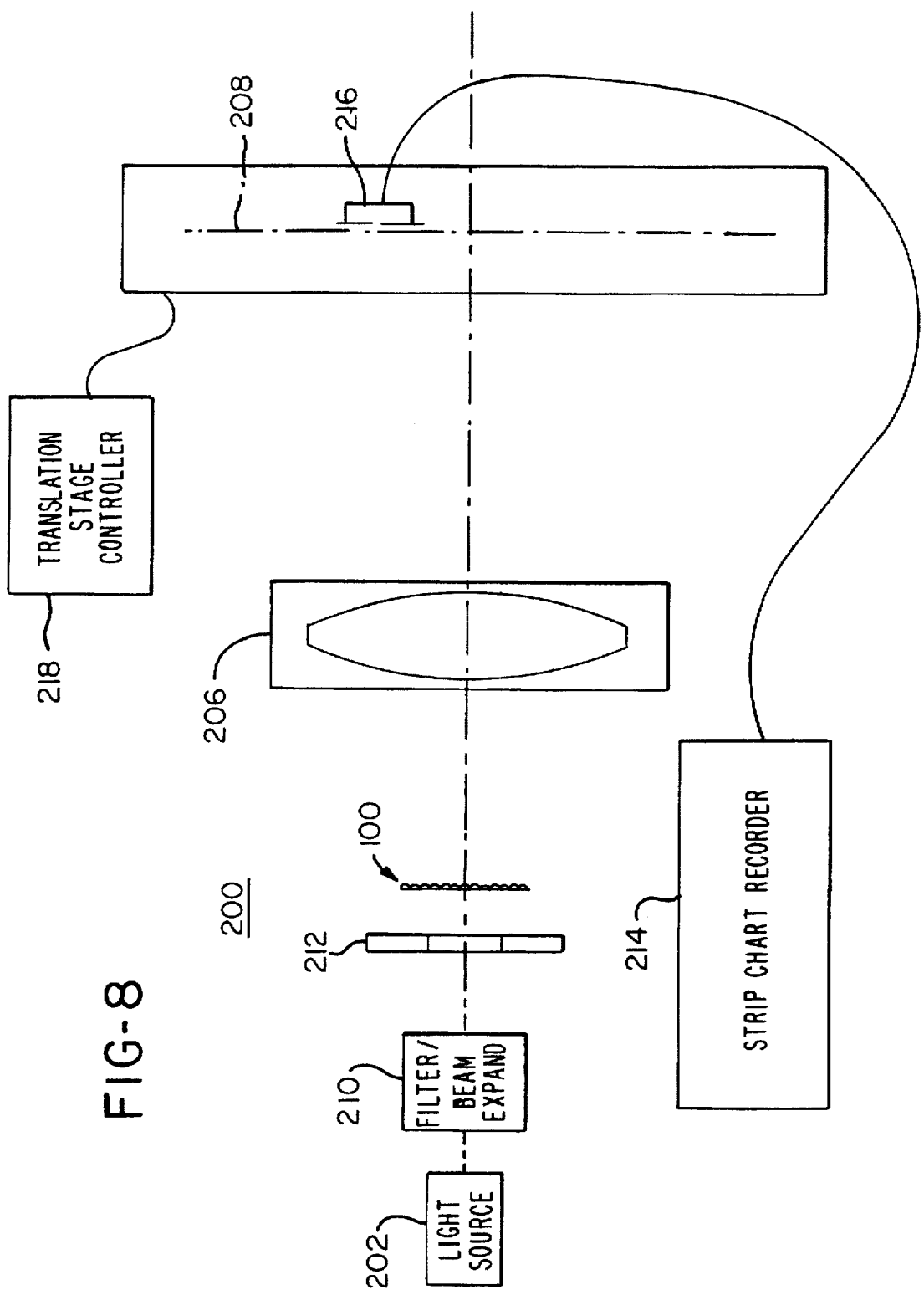
FIG. 8 schematically illustrates an apparatus layout for an optical fourier transform system operable in accordance with the present invention.

The invention of the present application will now be described with reference to the drawings wherein FIGS. 1 and 2 illustrate a lenticular array liquid sample container 100 which receives and holds a liquid sample to be analyzed. The sample container 100 containing the liquid sample is then placed into an optical fourier transform system, for example as shown in FIGS. 6–8, to generate a fourier transform image. The fourier transform image is representative of characteristics of the liquid sample contained within the container 100 and particles contained within the liquid sample.

The liquid sample container 100 comprises a microchanneled sample receiving and holding housing 102 defining a large plurality of parallel microchannels 104 having first open ends 104' and second open ends 104" with the parallel microchannels 104 lying in a plane. The housing 102 permits illumination of a sample received within the microchannels 104 along an optical axis A intersecting the microchannels 104. It is currently preferred to illuminate the sample along an optical axis A which is substantially perpendicular to the plurality of parallel open-ended microchannels 104 as illustrated; however, the invention will also operate if the sample is illuminated along axes oriented at angles other than 90° as will be apparent. It is also currently preferred to size the microchannels 104 for receiving a liquid sample therein by capillary action such that the microchannels 104 are shown larger than actual size in FIG. 1.

Figure 3:
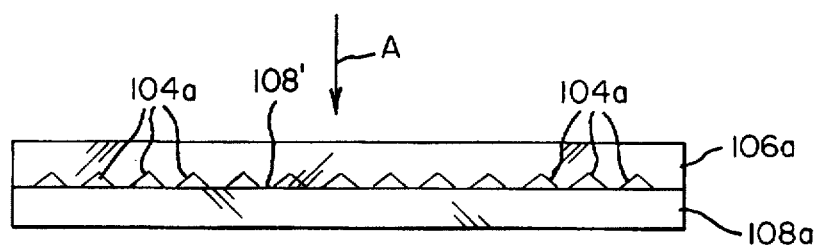
FIGS. 3, 4, 5 illustrate on a greatly exaggerated scale three different lenticular designs for use in the sample container of FIGS. 1 and 2.
Figure 4:
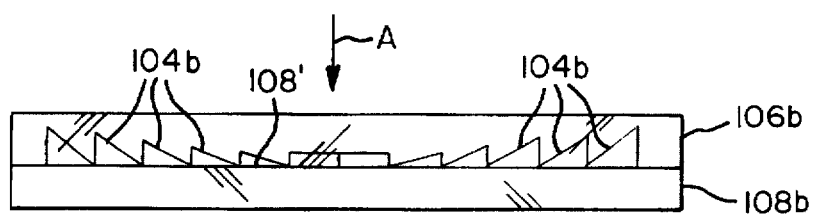
Figure 5:
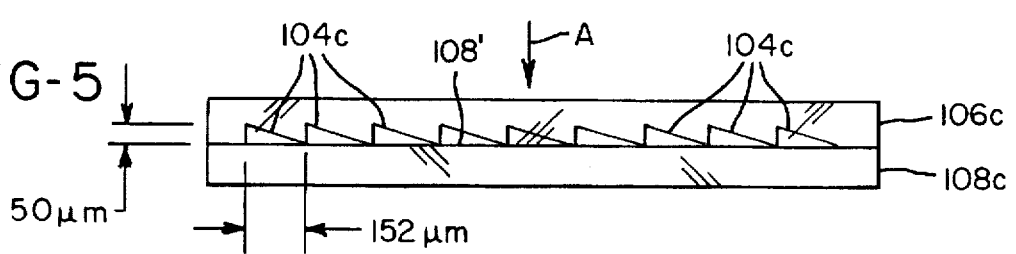

The microchannels 104 may have the same size and shape through the liquid sample container 100 or they may change incrementally along the array of the microchannels 104. For example, reference is made to FIGS. 3–5 which illustrate three different lenticular designs for use in the sample container 100. In particular, FIG. 3 illustrates what is referred to as a rod lenticular design wherein all of the microchannels 104a are the same along the array of the microchannels 104a. FIG. 4 illustrates what is referred to as a cylindrical fresnel lenticular design wherein the individual microchannels 104b vary in size and shape across the array of the microchannels 104b. FIG. 5 illustrates what is referred to as a prismatic lenticular design wherein all of the microchannels 104c are again the same along the array of the microchannels 104c. Representative sizing of the microchannels 104 of the sample container 100 is shown in FIG. 5 wherein each prismatic lenticular microchannel 104c is about 40 micrometers (µm) in depth and about 150 micrometers (µm) in width. This microchannel sizing or spacing produces a prism angle of about 18° which creates an approximately 9° optical deflection (refraction) angle.

The cross section of an individual microchannel is designed to allow for exposure of a representative percentage of all sizes of particles or cells within a liquid sample. To this end, the cross section of the microchannels are basically triangular for the illustrated designs. This allows for a range of mean optical path lengths through the container 100 from 0 to the height of the triangle. For example, in FIG. 3, the optical paths substantially continuously increase in optical path length from 0 at first sides of the microchannels 104c, the right sides in FIG. 3, to the heights of the triangles forming the microchannels 104c at second sides of the microchannels 104c, the left sides in FIG. 3. This can be seen in the three designs in FIGS. 3–5. The changing path lengths facilitate filling of the microchannels 104 by capillary action by providing a certain cross sectional area for the microchannels 104 for receiving given liquid samples. By tapering the sample receiving microchannels in a triangular design, exposure of a representative percentage of all sizes of particles or cells within a liquid sample is achieved. The liquid sample analysis using the containers does not count individual cells but parallel processes the frequency information in the sample and arrives at a one dimensional averaged display of the frequency information which yields statistical data on the liquid sample and particles or cells within the liquid sample as will be apparent from a review of the operation of the optical fourier transform system illustrated in FIGS. 6–8. While one dimensional fourier transform images are produced by a liquid sample in the microchannels 104, two dimensional fourier transform images can also be produced by the addition of generally perpendicular chemical strips within the microchannels.

The rod and prismatic designs of FIGS. 3 and 5 have between 100 and 200 identical redundant microchannels. The fresnel design of FIG. 4 has two redundant sets of varying microchannels. This redundancy offers the opportunity for designing in "control" channels, adding multiple tests to the sample container 100, or just taking advantage of the added precision that redundancy offers.

The sample container 100 is safe to the user in the sense that it has no sharp points or edges, is preferably made of plastic, and does not need to be centrifuged. It is low cost in that it consists of two plates which can be molded of plastic acrylic material. It is easy and simple to use in that a single drop of liquid is placed in a sample receiving recess from which it moves into the microchannels 104, preferably by capillary action. The container 100 is then placed in the instrument for analysis. After analysis, the container 100 is removed and disposed of with the sample contained therein.

The microchanneled sample receiving and holding housing 102 may be made of first and second plates molded or otherwise formed of optical quality acrylic or other appropriate optical material. If liquid samples contain moisture, it is preferred to coat or otherwise treat or construct the first and second plates to make them non-hydrophilic and thereby prevent moisture from being drawn from the sample by the container 100. For example, a glass film may be placed on the acrylic in a conventional manner. The first and second plates may also be coated with an appropriate chemical to facilitate use of the sample container for various immunoassay, kinematic diagnostic or other tests on liquid samples. Such chemical coating may be applied as strips generally perpendicular to the microchannels to generate two dimensional fourier transform images. Such chemical strips are preferably applied to the second plate 108.

The first plate 106 defines a lenticular element having a large plurality of microgrooves formed in a first surface thereof, the outwardly facing surface of FIG. 1. For example, the first surface of the lenticular element may have between 100 microgrooves and 200 microgrooves per inch. The second plate 108 is at least coextensive with a portion of the first plate 106 having the microgrooves and defines a surface 108' for engaging that portion of the first plate 106 to close the microgrooves to thereby define the open-ended microchannels 104. Working liquid sample containers were made using commercially available components from vendors such as Fresnel Optics, Inc. of Rochester, N.Y.

The second plate 108 is secured to the first plate 106 by means of a solvent adhesive or as is otherwise appropriate for a given optical material. The second plate 108 is aligned with the first plate 106 by means of pins 110 extending from the surface of the first plate 106 which are received in matching openings 112 through the second plate 108. The first plate 106 extends beyond the first ends 104' of the open-ended microchannels 104 to define a sample loading member 106' for receiving a liquid sample to be loaded into the microchannels 104.

The sample loading member 106' defines a recess 114 for receiving a liquid sample to be loaded into the microchannels 104 and carrying the sample to the first ends 104' of the plurality of parallel open-ended microchannels 104. In the illustrated embodiment, the recess 114 is generally keyhole shaped having a generally circular sample receiving portion 116 and a sample conveying channel 118 extending from the circular sample receiving portion 116 to the first ends 104' of the plurality of open-ended microchannels 104. The sample loading member 106' also defines a handle 120 for holding and handling the container 100. The first plate 106 also defines a vent channel 122 for venting the second open ends 104" of the plurality of microchannels 104 to allow air to escape and to contain and stabilize movement of the sample once inside the microchannels 104. For this embodiment, an appropriate chemical to facilitate use of the sample container 100 for various immunoassay, kinematic diagnostic or other tests on liquid samples, as noted earlier, may be coated onto the circular sample receiving portion 116, the sample conveying channel 118 and/or the open-ended microgrooves which are covered to form the microchannels 104.

After a liquid sample to be analyzed has been loaded into a liquid sample container, such as the liquid sample container 100 as described above, the liquid sample container is placed into an optical fourier transform system 200 as shown in FIGS. 6–8. The optical fourier transform system 200 includes a light source 202 which generates spatially coherent, quasimonochromatic waves, such as plane waves 204 which emanate from a laser or a collimated, filtered Hg arc source. While a variety of light sources and lasers can be used in the optical fourier transform system, a laser diode is preferred because of its low cost and power requirements which allows the system 200 to be operated from battery power and hence to be portable. The light plane waves 204 illuminate the sample received within the microchannels 104 of the liquid sample container 100 along an optical axis A intersecting the microchannels 104 of the liquid sample container 100 with the liquid sample container 100 serving as a grating of the optical fourier transform system 200. A transform lens 206 receives light which has been transmitted through the liquid sample container 100 and focuses or generates a spatial frequency pattern or optical fourier transform image of the received light at a fourier transform plane 208.

FIG. 8 schematically illustrates an apparatus layout for an optical fourier transform system 200 operable in accordance with the invention of the present application. The light source 202 comprises a 670 nm red laser diode which is passed through a spatial filter/beam expander 210 and a 0.5 inch diameter iris 212 to illuminate the sample container 100. Data is collected from the fourier transform plane 208 by means of a strip chart recorder 214 from a slit detector 216 which is translated through the fourier transform image by a translation stage controller 218.

Figure 9:
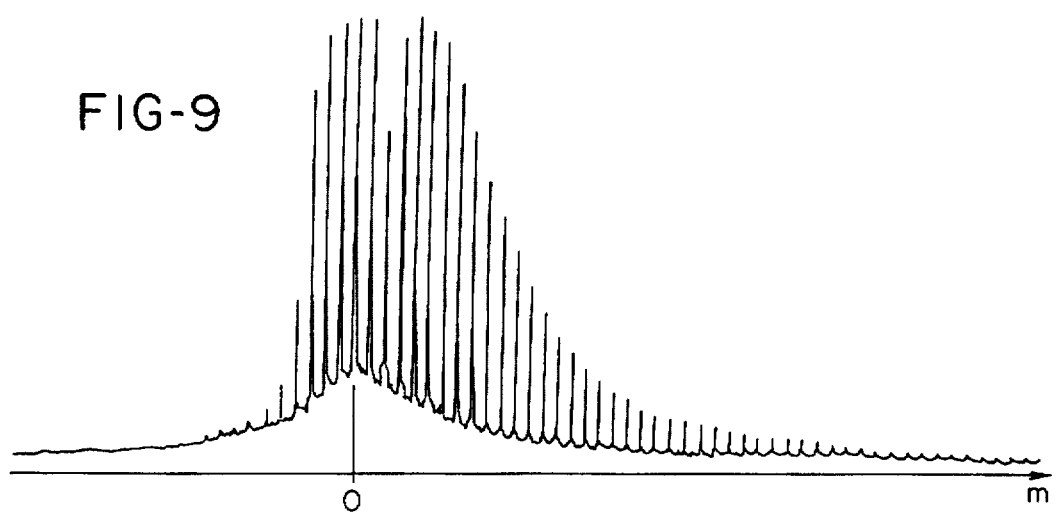
FIGS. 9, 10, 11 illustrate data obtained from the optical fourier transform system of FIG. 8 for whole blood, dense whole blood red cells, and blood white cells and platelets, respectively.
Figure 10:
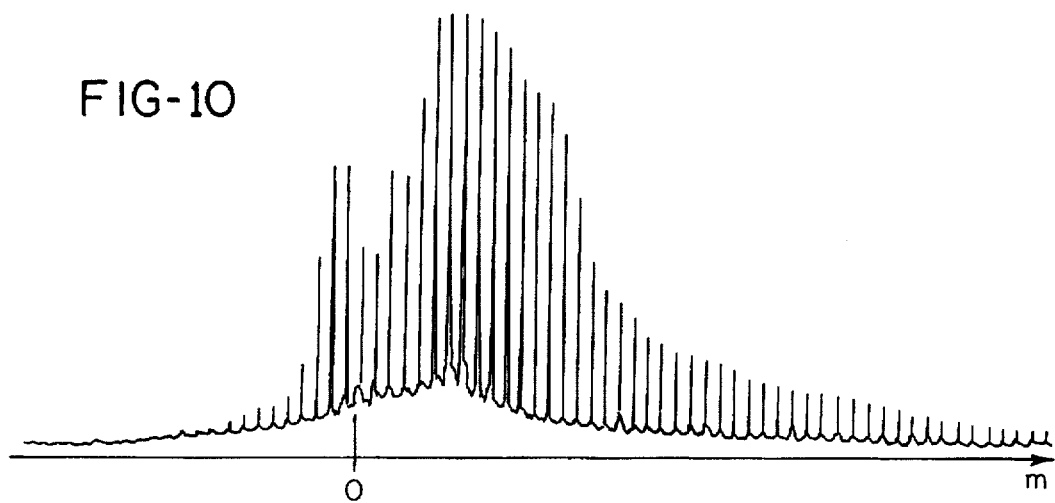
Figure 11:
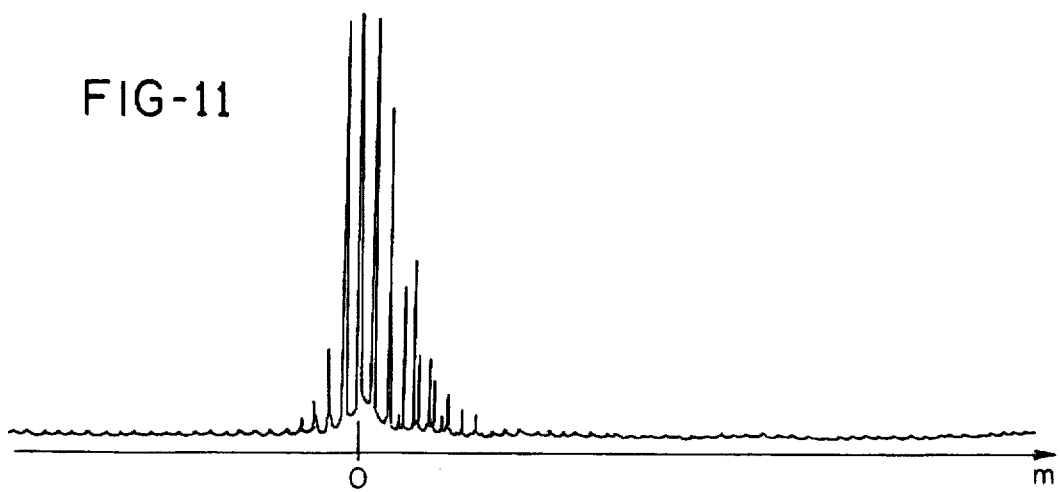

FIGS. 9–11 illustrate data which was collected via the strip chart recorder 214 for liquid samples comprising whole blood, dense whole blood red cells and blood white cells and platelets, respectively. The liquid sample containers used to collect this data were of the prismatic lenticular design illustrated in FIG. 5 and had a facet spacing of 0.15 millimeters (mm), 167 prisms per inch, and an optical deflection angle of 9°. It is apparent from these human blood samples that unique fourier transform images or signatures are obtained. While further refinement of the analysis of the fourier transform signatures is ongoing, it is believed that a statistical determination of the size, shape, density, and regularity of cells within samples will be provided by the spatial data in the fourier transform signatures.

The strip chart fourier transform signature obtained for whole blood using the system 200 of FIG. 8 is shown if FIG. 9. This signature lacks high order signals to the left of center, m=0. This characteristic was also observed in signatures obtained for sample solutions including suspensions of 4.5 μm microspheres. There is also an asymmetry about the zero order, m=0, and a secondary peak around m=4 to the right of zero order.

The whole blood was allowed to set for a few hours so gravity would somewhat separate the cell types within the blood. An optical fourier transform signature for dense whole blood red cells was then obtained, as shown in FIG. 10, by sampling from the bottom of the whole blood. The signature of FIG. 10 shows a side peak at m=−7, i.e. to the left of zero, no minor peak to the right of zero, and still no high order signals to the left of zero. Some very small signal peaks are also present between the major orders around zero order. These characteristics were also observed in signatures obtained for sample solutions including suspensions of 15 μm and 4.5 μm microspheres.

The strip chart fourier transform signature obtained for predominantly white cells and platelets using the system 200 of FIG. 8 is shown if FIG. 11. An important feature of the signature of FIG. 11 is the fairly strong signal between m=3 and m=4 to the right of zero order. This characteristic was also present, although much weaker, in signatures obtained for sample solutions including suspensions of 4.5 μm and 15 μm microspheres. High order signals immediately to the left of zero order are also present. This signature has significantly different features than the signatures of whole blood of FIGS. 9 and 10.

An advantage of the prismatic lenticular sample container is that the location of the zero order, m=0, with respect to the optical axis A is directly effected by the index of refraction of the sample. This is a clinically useful measurement for protein determination. This may also explain the unusual peak in the white cells and platelets signature of FIG. 11. However, to confirm this it is necessary to know the index of refraction of white cells and platelets.

Figure 12:
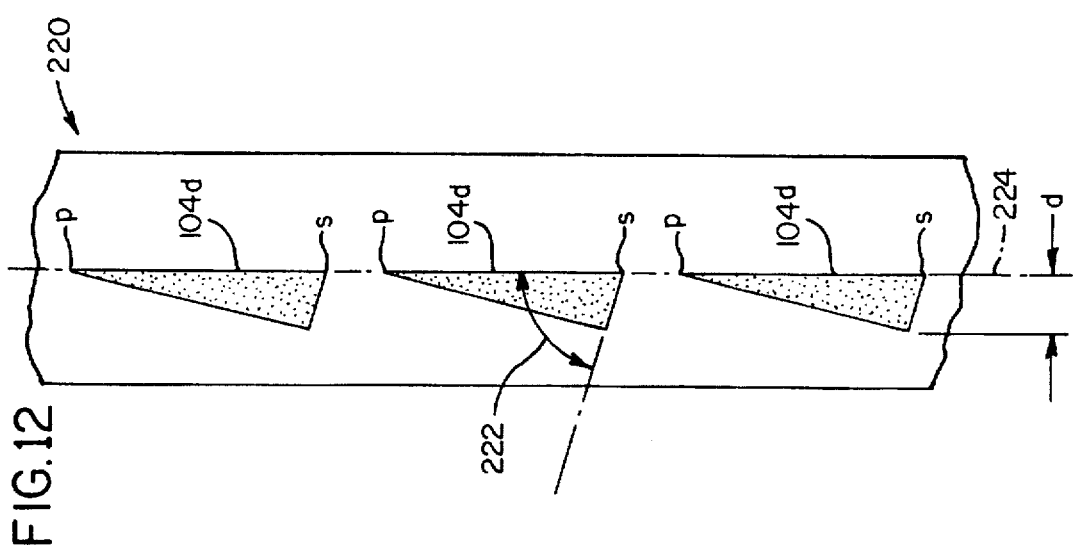
FIG. 12 illustrate on a greatly exaggerated scale an additional lenticular design for use in the sample container of FIGS. 1 and 2.

An additional lenticular design for use in the sample container 100 is illustrated in FIG. 12. In particular, FIG. 12 illustrates a prismatic lenticular array 220 wherein all of the microchannels 104d are the same along the array of the microchannels 104d and the microchannels 104d are spaced from one another by a defined spacing. The defined spacing between the microchannels 104d as illustrated and currently preferred is approximately equal to the maximum depth d of the microchannels 104d; however, other defined spacing is possible in the present invention.

The lenticular design of FIG. 12 results in an additional optical fourier transform image of the received light at a fourier transform plane and, hence, additional information for analysis of the sample contained in the microchannels 104d. In particular, the spaced design of FIG. 12 results in a fourier pattern, which is referred to herein as a "diffracted" optical fourier transform image df, in addition to the "refracted" optical fourier transform image rf of the previously described lenticular designs, see FIGS. 13 and 14. The energy distribution in the transform df is a function of diffraction from the edges of the microchannels 104d. One edge is the tapered point p of a first side of each microchannel 104d and the other edge is the deep side s of each adjacent microchannel 104d of a second side of each microchannel 104d. The resulting pattern is asymmetrical but independent of the index of refraction of the sample in the microchannels 104d.

A third fourier transform image can be obtained by angling the deep or second side of each microchannel 104d so that it presents an optical interface to the illuminating plane wave at an angle near the critical angle for total internal reflection (TIR) given the nominal index of refraction for the sample. That is, the second sides of the microchannels 104d are angled at an acute angle 222 relative to the plane 224 of the microchannels 104d.

Figure 13:
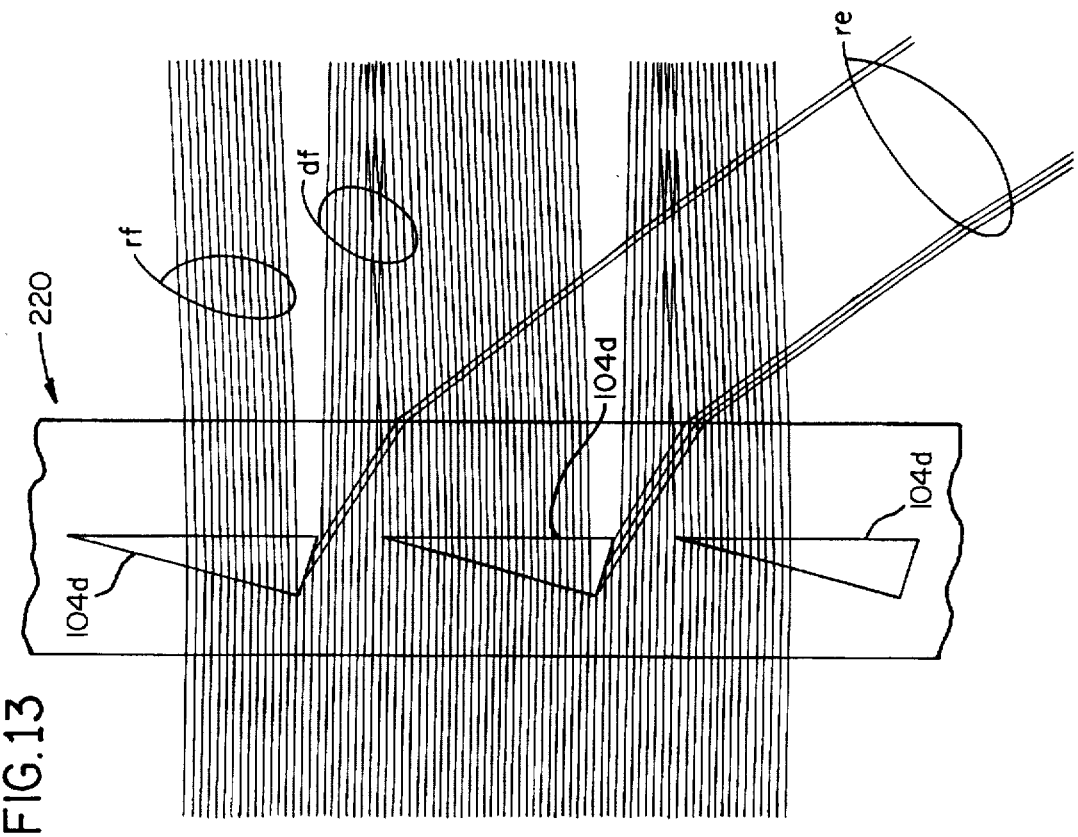
FIG. 13 illustrates formation of refracted, diffracted and reflected optical fourier transform images using the lenticular design of FIG. 12.

Light reflected from the angled second sides of the microchannels 104d passes through the clear openings defined by the spacings between the microchannels 104d and results in the third fourier transform image which is referred to herein as a fourier transform of total internal reflection or "reflected" optical fourier transform image re, see FIGS. 13 and 14, and is a function of the refractive index of the sample in the microchannels 104d. The reflected optical fourier transform image re may be monitored as the incident angle of illumination is incrementally changed for mapping the refractive index of the sample components.

The illustrated components of the schematic apparatus layout of an optical fourier transform system 200a of FIG. 14 which are the same as those of FIG. 8 have been identified by the same numerals but with the suffix "a". In addition to these components, a second transform lens 206b has been added to receive light which has been reflected through the liquid sample container to generate the reflected optical fourier transform image re as described above.

Another aspect of the present invention is the transition from one dimensional fourier transform images to two dimensional fourier transform images with the accompanying increased analysis information the two dimensional fourier transform images makes available. Such a transition can be made by forming a plurality of parallel chemical compound strips within the optical lenticular array or microchannels with the parallel chemical strips being oriented generally perpendicular to the microchannels. Spacing for the strips is currently preferred to be approximately the same as the spacing of the microchannels; however, other spacings are possible in the present invention. Chemical compound used to form the strips can be, for example, an appropriate antigen for a sample to be analyzed.

Figure 16:
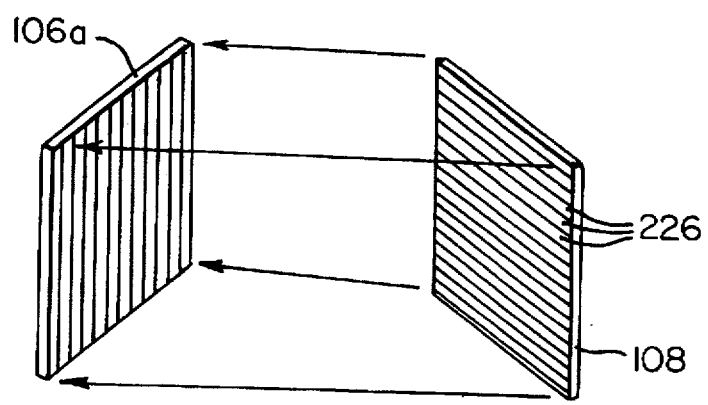
FIG. 16 illustrates a chemically striped second plate utilized to make a liquid sample container capable of producing two dimensional fourier transform images in accordance with the present invention.

The chemical strips can be coated within the microchannels in any appropriate manner for example by striping the microgrooves in the first plate 106 or by striping the second plate 108. For ease of construction, it is currently preferred to stripe the second plate 108 with chemical strips 226 such that the second plate 108 can then be assembled to a first plate 106a to convert the microgrooves in the first plate 106a to the microchannels 104, see FIG. 16.

In any event, the resulting two dimensional fourier transform images are represented by a two dimensional fourier transform image 228 in FIG. 15. The chemical reaction with the sample, for example an antigen-antibody reaction, can then be monitored in the two dimensional fourier transform image 228 such that the container functions as a diagnostic immunoassay. Note that the chemical reaction is primarily monitored in the refracted optical fourier transform image rf since the other two optical fourier transform images are less sensitive to the chemical reaction.

Having thus described the invention of the present application in detail and by reference to preferred embodiments thereof, it will be apparent that modifications and variations are possible without departing from the scope of the invention defined in the appended claims.

What is claimed is:

1. A liquid sample container for an optical fourier transform system, said liquid sample container comprising a housing defining a plurality of parallel open-ended sample receiving and holding optical microchannels lying adjacent one another within a plane to form an optical lenticular array, each of said optical microchannels defining a plurality of optical paths through said microchannel which optical paths continuously increase in optical path length from a minimum path length at a first side of said microchannel to a maximum path length at a second side of said microchannel, said housing permitting illumination of a liquid sample received and held within said microchannels along an optical axis intersecting said plane at an angle other than zero degrees, said housing being substantially transparent to said illumination so that said illumination passes entirely through said housing and said liquid sample held within said microchannels without being impeded by said housing wherein said illumination forms a fourier transform image at a fourier transform plane of said optical fourier transform system.

2. A liquid sample container as claimed in claim 1 wherein said optical axis is generally perpendicular to said plane.

3. A liquid sample container as claimed in claim 1 wherein said liquid sample container is non-hydrophilic.

4. A liquid sample container as claimed in claim 1 wherein said parallel open-ended microchannels have right triangular cross sections.

5. A liquid sample container as claimed in claim 1 wherein said housing comprises:
a first plate having a plurality of parallel microgrooves formed in a first surface thereof; and
a second plate at least coextensive with a portion of said first plate having said microgrooves and defining a surface for engaging said portion of said first plate to close said microgrooves to thereby define said open-ended sample receiving and holding optical microchannels.

6. A liquid sample container as claimed in claim 5 wherein said of sample receiving and holding optical microchannels have first and second open ends, and said first plate extends beyond said first open ends of said open-ended sample receiving and holding optical microchannels to define a liquid sample loading member for receiving a liquid sample to be loaded into said microchannels.

7. A liquid sample container as claimed in claim 6 wherein said first plate defines an open vent channel for venting said second open ends of said plurality of microchannels.

8. A liquid sample container as claimed in claim 1 wherein said housing includes a liquid sample loading member extending beyond one end of said plurality of parallel open-ended optical microchannels for receiving a liquid-sample to be loaded into said microchannels.

9. A liquid sample container as claimed in claim 1 further comprising a plurality of parallel chemical strips formed within said optical lenticular array, oriented generally perpendicular thereto and spaced for producing a two dimensional fourier transform image upon illumination of a sample held within said sample container.

10. A liquid sample container as claimed in claim 9 wherein said chemical strips are formed of an antigen.

11. A liquid sample container for an optical fourier transform system, said liquid sample container comprising a housing defining a plurality of parallel open-ended sample receiving and holding optical microchannels extending in a first direction and lying within a plane and a plurality of parallel chemical strips formed within said sample container and oriented generally perpendicular to said microchannels, said housing permitting illumination of a liquid sample received within said microchannels along an optical axis intersecting said plane at an angle other than zero degrees wherein said plurality of chemical strips are spaced so that said illumination forms a two dimensional fourier transform image at a fourier transform plane of said optical fourier transform system.

12. A liquid sample container as claimed in claim 11 wherein said housing comprises:
  a first plate having a plurality of parallel microgrooves formed in a first surface thereof; and
  a second plate at least coextensive with a portion of said first plate having said microgrooves and defining a surface for engaging said portion of said first plate to close said microgrooves to thereby define said open-ended sample receiving and holding optical microchannels, said surface of said second plate being coated to define said chemical strips.

13. A liquid sample container comprising a housing defining a plurality of parallel open-ended sample receiving and holding optical microchannels extending in a first direction and lying within a plane, said microchannels being spaced from one another by a defined spacing and said housing permitting illumination of a liquid sample received and held within said microchannels along an optical axis intersecting said plane at an angle other than zero degrees, said housing being substantially transparent to said illumination so that said illumination passes entirely through said housing and said liquid sample held within said microchannels without being impeded by said housing, said defined spacing forming clear openings between said microchannels.

14. A liquid sample container as claimed in claim 13 wherein each of said microchannels defines a plurality of optical paths through said microchannel which optical paths continuously increase in optical path length from a minimum path length at a first side of said microchannel to a maximum path length at a second side of said microchannel.

15. A liquid sample container as claimed in claim 14 wherein said defined spacing is approximately equal to said maximum path length.

16. A liquid sample container as claimed in claim 15 wherein said second sides of said microchannels are acutely angled relative to said plane, said clear openings between said microchannels passing light reflected from said second sides of said microchannels upon illumination of a sample within said sample container.

17. A liquid sample container as claimed in claim 16 further comprising a plurality of parallel chemical strips formed within said sample container, oriented generally perpendicular to said microchannels and spaced for producing a two dimensional fourier transform image upon illumination of a sample held within said sample container.

18. A liquid sample container for an optical fourier transform system said liquid sample container comprising a housing defining a plurality of substantially equally spaced parallel open-ended sample receiving and holding optical microchannels extending in a first direction and lying within a plane, each of said microchannels defining a plurality of optical paths through said microchannel which optical paths continuously increase in optical path length from a minimum path length at a first side of said microchannel to a maximum path length adjacent a second side of said microchannel and which second side of said microchannel is acutely angled relative to said plane at an angle near the critical angle for total internal reflection given a nominal index of refraction for a sample to be received within said liquid sample container, said housing permitting illumination of a liquid sample received and held within said microchannels along an optical axis intersecting said plane at an angle other than zero degrees, said housing being substantially transparent to said illumination so that said illumination passes entirely through said housing and said liquid sample held within said microchannels without being impeded by said housing wherein said illumination forms a fourier transform image at a fourier transform plane of said optical fourier transform system.

19. A liquid sample container as claimed in claim 18 further comprising a plurality of parallel chemical strips formed within said sample container, oriented generally perpendicular to said microchannels and spaced for producing a two dimensional fourier transform image upon illumination of a sample held within said sample container.

20. A liquid sample container as claimed in claim 19 wherein said housing comprises:
  a first plate having a plurality of parallel microgrooves formed in a first surface thereof; and
  a second plate at least coextensive with a portion of said first plate having said microgrooves and defining a surface for engaging said portion of said first plate to close said microgrooves to thereby define said open-ended sample receiving and holding optical microchannels, said surface of said second plate being coated to define said chemical strips.

21. A method of analyzing a liquid sample comprising the steps of:
  depositing a liquid sample to be analyzed into a housing having a plurality of parallel open-ended sample receiving and holding optical microchannels lying within a plane and forming a lenticular array, said microchannels being spaced from one another by a defined spacing;
  illuminating said liquid sample receiving and holding housing along an optical axis intersecting said plane within which said plurality of parallel open-ended sample receiving and holding optical microchannels lie at an angle greater than zero relative to said plane;
  focusing light received from said liquid sample receiving and holding housing onto a fourier transform plane; and
  detecting at least one optical fourier transform at said fourier transform plane.

22. A method of analyzing a fluid sample as claimed in claim 21 further comprising the step of determining characteristics of said fluid sample by analyzing said at least one optical fourier transform.

23. A method of analyzing a fluid sample as claimed in claim 21 wherein said step of detecting at least one optical fourier transform comprises the step of detecting a refracted optical fourier transform and a diffracted optical fourier transform.

24. A method of analyzing a fluid sample as claimed in claim 21 wherein said microchannels define a plurality of optical paths which continuously increase in optical path length from a minimum path length at a first side of said microchannel to a maximum path length at a second side of said microchannel which is acutely angled relative to said plane and said step of detecting at least one optical fourier transform comprises the step of detecting a reflected optical fourier transform.

25. A method of analyzing a fluid sample as claimed in claim 21 wherein said housing further comprises a plurality of parallel chemical strips formed within said lenticular array and oriented generally perpendicular thereto and said step of detecting at least one optical fourier transform comprises the step of detecting at least one two dimensional optical fourier transform.

26. A liquid sample container as claimed in claim 11 wherein said chemical strips are spaced approximately the same as spacing of said microchannels.

* * * * *

UNITED STATES PATENT AND TRADEMARK OFFICE
CERTIFICATE OF CORRECTION

PATENT NO. : 5,760,894
DATED : June 2, 1998
INVENTOR(S) : Mersch

It is certified that error appears in the above-identified patent and that said Letters Patent is hereby corrected as shown below:

Col. 12, line 8, "transform system said" should read --transform system, said--

Signed and Sealed this

Twenty-ninth Day of September, 1998

Attest:

BRUCE LEHMAN

Attesting Officer

Commissioner of Patents and Trademarks